US008629334B2

(12) United States Patent
Dawson et al.

(10) Patent No.: US 8,629,334 B2
(45) Date of Patent: Jan. 14, 2014

(54) VIRAL-BASED TRANSIENT-EXPRESSION VECTOR SYSTEM FOR TREES

(75) Inventors: William O. Dawson, Winter Haven, FL (US); Svetlana Y. Folimonova, Winter Haven, FL (US); Alexey S. Folimonov, Moscow (RU)

(73) Assignee: University of Florida Research Foundation, Inc., Gainesville, FL (US)

( * ) Notice: Subject to any disclaimer, the term of this patent is extended or adjusted under 35 U.S.C. 154(b) by 812 days.

(21) Appl. No.: 12/174,159

(22) Filed: Jul. 16, 2008

(65) Prior Publication Data

US 2010/0017911 A1 Jan. 21, 2010

(51) Int. Cl.

| | |
|---|---|
| ***A01H 5/00*** | (2006.01) |
| ***A01H 9/00*** | (2006.01) |
| ***C12N 15/82*** | (2006.01) |

(52) U.S. Cl.
USPC ......... 800/316; 800/295; 800/278; 435/320.1

(58) Field of Classification Search
None
See application file for complete search history.

(56) References Cited

U.S. PATENT DOCUMENTS

| | | | | |
|---|---|---|---|---|
| 4,517,177 | A | 5/1985 | Markham et al. | |
| 5,141,742 | A | 8/1992 | Brown et al. | |
| 5,770,442 | A | 6/1998 | Wickham et al. | |
| 5,804,177 | A | 9/1998 | Humphries | |
| 5,817,492 | A | 10/1998 | Saito et al. | |
| 5,824,485 | A | 10/1998 | Thompson et al. | |
| 5,843,459 | A | 12/1998 | Wang et al. | |
| 6,197,948 | B1 | 3/2001 | Zhu et al. | |
| 6,287,814 | B1 | 9/2001 | Hope et al. | |
| 6,916,970 | B2 * | 7/2005 | Liang et al. | 800/279 |
| 2008/0118521 | A1 | 5/2008 | Spring et al. | |
| 2008/0118979 | A1 | 5/2008 | Draper et al. | |
| 2008/0119433 | A1 | 5/2008 | Tabor | |
| 2008/0127375 | A1 | 5/2008 | Ali et al. | |

FOREIGN PATENT DOCUMENTS

| | | |
|---|---|---|
| EP | 1757702 | 2/2007 |
| EP | 1757703 | 2/2007 |
| EP | 1816203 | 4/2008 |

OTHER PUBLICATIONS

Robertson et al. 2005, Sixteenth IOCV Conference p. 187-195.*
Gowda et al. 2000, Virology 274:246-254.*
Ayllon et al. 2005, Molecular Plant Pathology 6:165-176.*
Peremyslov et al. 1999, PNAS 14771-14776.*
Folimonov et al. 2007 Virology 368:205-216.*
Agranovsky, A.A., 1996. Principles of molecular organization, expression, and evolution of closteroviruses: over the barriers. Adv. Virus Res. 47, 119-158.
Albiach-Martí, M.R., Mawassi, M., Gowda, S., Satyanarayana, T., Hilf, M.E., Shanker, S., Almira, E.C., Vives, M.C., Lopez, C., Guerri, J., Flores, R., Moreno, P., Garnsey, S.M., Dawson, W.O., 2000. Sequences of *Citrus tristeza virus* separated in time and space are essentially identical. J.Virol. 74, 6856-6865.
Alzhanova, D.V., Napuli, A.J., Creamer, R., Dolja, V.V., 2001. Cell-to-cell movement and assembly of a plant closterovirus: roles for the capsid proteins and Hsp70 homolog. EMBO J. 20, 6997-7007.
Arazi, T., Lee Huang, P., Huang, P.L., Zhang, L., Moshe Shiboleth, Y., Gal-On, A., Lee-Huang, S., 2002. Production of antiviral and antitumor proteins MAP30 and GAP31 in cucurbits using the plant virus vector ZYMV-AGII. Biochem. Biophys. Res. Commun. 292, 441-448.
Atkinson, R.G., Bieleski, L.R.F., Gleave, A.P., Janssen, B.J., Morris, B.A.M., 1998. Post-transcriptional silencing of chalcone synthase in *Petunia* using a geminivirus-based episomal vector. Plant J. 15, 593-604.
Ayllón, M.A., Gowda, S., Satyanarayana, T., Karasev, A.V., Adkins, S., Mawassi, M., Guerri, J., Moreno, P., Dawson, W.O., 2003. Effects of modification of the transcription initiation site context on *Citrus tristeza virus* subgenomic RNA synthesis. J. Virol. 77, 9232-9243.
Ayllón, M.A., Gowda, S., Satyanarayana, T., Dawson, W.O., 2004. cis-acting elements at opposite ends of the *Citrus tristeza virus* genome differ in initiation and termination of subgenomic RNAs. Virology 322, 41-50.
Ayllón, M.A., Satyanarayana, T., Gowda, S., Dawson, W.O., 2005. An atypical 3'-controller element mediates low-level transcription of the p6 subgenomic mRNA of *Citrus tristeza virus*. Mol. Plant Pathol. 6, 165-176. Bar-Joseph, M., Garnsey, S.M., Gonsalves, D., 1979. The closteroviruses: a distinct group of elonoated plant viruses. Adv. Virus Res. 25. 93-168.
Chapman, S., Kavanagh, T., Baulcombe, D., 1992. *Potato virus X* as a vector for gene expression in plants. Plant J. 2, 549-557.
Culver, J.N., 1996. Tobamovirus cross protection using a potexvirus vector. Virology 226, 228-235.
Dawson, W.O., Bubrick, P., Grahtham, G.L., 1988. Modifications of the tobacco mosaic virus coat protein gene affecting replication, movement, and symptomatology. Phytopathology 78, 783-789.
Dawson, W.O., Lewandowski, D.J., Hilf, M.E., Bubrick, P., Raffo, A.J., Shaw, J.J., Grantham, G.L., Desjardins, P.R., 1989. A *Tobacco mosaic virus*-hybrid expresses and loses an added gene. Virology 172, 285-292.

(Continued)

*Primary Examiner* — Li Zheng
(74) *Attorney, Agent, or Firm* — Timothy H. Van Dyke; Beusse, Wolter, Sanks, Mora & Maire, P.A.

(57) ABSTRACT

Disclosed herein are viral vectors suitable for transfection into woody trees for purposes of delivering and expressing beneficial genes with increased stability. Specifically exemplified herein are vectors for transfecting citrus trees. The vectors allow for the expression of useful proteins, such as those that can protect the tree from disease.

13 Claims, 4 Drawing Sheets

(56) References Cited

OTHER PUBLICATIONS

Dolja, V.V., Karasev, A.V., Koonin, E.V., 1994. Molecular biology and evolution of closteroviruses: sophisticated build-up of large RNA genomes. Annu. Rev. Phytopathol. 32, 261-285.
Donnelly, M.L.L., Hughes, L.E., Luke, G., Mendoza, H., ten Dam, E., Gani, D., Ryan, M.D., 2001a. The 'cleavage' activities of *Foot-and-mouth disease virus* 2A site-directed mutants and naturally occurring '2A-like' sequences. J. Gen. Virol. 82, 1027-1041.
Donnelly, M.L., Luke, G., Mehrotra, A., Li, X., Hughes, L.E., Gani, D., Ryan, M.D., 2001b. Analysis of the aphthovirus 2A/2B polyprotein 'cleavage' mechanism indicates not a proteolytic reaction, but a novel translational effect: a putative ribosomal 'skip'. J. Gen. Virol. 82, 1013-1025.
Donson, J., Kearney, C.M., Hilf, M.E., Dawson, W.O., 1991. Systemic expression of a bacterial gene by a *Tobacco mosaic virus*-based vector. Proc. Natl. Acad. Sci. USA 88, 7204-7208.
French, R., Janda, M., Ahlquist, P., 1986. Bacterial gene inserted in an engineered RNA virus: efficient expression in monocotyledonous plant cells. Science 231, 1294-1297.
Garnsey, S.M., Cambra, M., 1991. Enzyme-linked immunosorbent assay (ELISA) for *Citrus* pathogens. In: Roistacher, C.N. (Ed.), Graft-Transmissible Diseases of *Citrus*, Handbook for Detection and Diagnosis. FAO, Rome, pp. 193-216.
Gowda, S., Satyanarayana, T., Davis, C.L., Navas-Castillo, J., Albiach-Marti, M.R., Mawassi, M., Valkov, N., Bar-Joseph, M., Moreno, P., Dawson, W.O., 2000. The p20 gene product of *Citrus tristeza virus* accumulates in the amorphous inclusion bodies. Virology 274, 246-254.
Gowda, S., Satyanarayana, T., Ayllón, M.A., Albiach-Martí, M.R., Mawassi, M., Rabindran, S., Garnsey, S.M., Dawson, W.O., 2001. Characterization of the *cis*-acting elements controlling subgenomic mRNAs of *Citrus tristeza virus*: production of positive- and negative-stranded 3'-terminal and positive-stranded 5'-terminal RNAs. Virology 286, 134-151.
Grdzelishvili, V.Z., Chapman, S.N., Dawson, W.O., Lewandowski, D.J., 2000. Mapping of the *Tobacco mosaic virus* movement protein and coat protein subgenomic RNA promoters in vivo. Virology 275, 177-192.
Skuzeski, James M., Jendrisak, Jerry J., 1985 A Family of wheat embryo U2 snRNAs. Plant Molecular Biology, 181-193.
Higuchi, R., Krummel, B., Saiki, R.K., 1988. A general method of in vitro preparation and specific mutagenesis of DNA fragments: study of protein and DNA interactions. Nucleic Acids Res. 16, 7351-7367.
Hilf, M.E., Karasev, A.V., Pappu, H.R., Gumpf, D.J., Niblett, C.L., Garnsey, S.M., 1995. Characterization of *Citrus tristeza virus* subgenomic RNAs in infected tissue. Virology 208, 576-582.
Ion-Nagy, L., Lansac, M., Eyquard, J.P., Salvador, B., Garcia, J.A., Le Gall, O., Hernould, M., Schurdi-Levraud, V., Decroocq, V., 2006. PPV long-distance movement is occasionally permitted in resistant apricot hosts. Virus Res.120, 70-78.
Johnson, J.A., Bragg, J.N., Lawrence, D.M., Jackson, A.O., 2003. Sequence elements controlling expression of *Barley stripe mosaic virus* subgenomic RNAs in vivo. Virology 313, 66-80.
Karasev, A.V., 2000. Genetic diversity and evolution of closteroviruses. Annu. Rev. Phytopathol. 38, 293-324.
Karasev, A.V., Boyko, V.P., Gowda, S., Nikolaeva, O.V., Hilf, M.E., Koonin, E.V., Niblett, C.L., Cline, K., Gumpf, D.J., Lee, R.F., Garnsey, S.M., Lewandowski, D.J., Dawson, W.O., 1995. Complete sequence of the *Citrus tristeza virus* RNA genome. Virology 208, 511-520.
Karasev, A.V., Hilf, M.E., Garnsey, M.E., Dawson, W.O., 1997. Transcriptional strategy of closteroviruses: mapping the 5' termini of the *Citrus tristeza virus* subgenomic RNAs. J. Virol. 71, 6233-6236.
Kumagai, M.H., Turpen, T.H., Weinzettl, N., della-Cioppa, G., Turpen, A.M., Donson, J., Hilf, M.E., Grantham, G.L., Dawson, W.O., Chow, T.P., Piatak, M., Jr., Grill, L.K., 1993. Rapid, high-level expression of biologically active alpha-trichosanthin in transfected plants by an RNA viral vector. Proc. Natl. Acad. Sci. USA 90, 427-430.
Kumagai, M.H., Donson, J., della-Cioppa, G., Harvey, D., Hanley, K., Grill, L.K., 1995. Cytoplasmic inhibition of carotenoid biosynthesis with virus-derived RNA. Proc. Natl. Acad. Sci. USA 92, 1679-1683.
Kumagai, M.H., Keller, Y., Bouvier, F., Clary, D., Camara, B., 1998. Functional integration of non-native carotenoids into chloroplasts by viral-derived expression of capsanthin-capsorubin synthase in *Nicotiana benthamiana* . Plant J.14, 305-315.
Lansac, M., Eyquard, J.P., Salvador, B., Garcia, J.A., Le Gall, O., Decroocq, V., Schurdi-Levraud, V., 2005. Application of GFP-tagged *Plum pox virus* to study *Prunus*-PPV interactions at the whole plant and cellular levels. J. Virol. Methods 129, 125-133.
Lu, R., Folimonov, A., Shintaku, M., Li, W.X., Falk, B.W., Dawson, W.O., Ding, S.W., 2004. Three distinct suppressors of RNA silencing encoded by a 20-kb viral RNA genome. Proc. Natl. Acad. Sci. USA 101, 15742-15747.
Mawassi, M., Mietkiewska, E., Hilf, M.E., Ashoulin, L., Karasev., A.V., Gafny, R., Lee, R.F., Garnsey, S.M., Dawson, W.O., Bar-Joseph, M., 1995. Multiple species of defective RNAs in plants infected with *Citrus tristeza virus*. Virology 214, 264-268.
McCormick, A.A., Kumagai, M.H., Hanley, K., Turpen, T.H., Hakim, I., Grill, L.K., Tuse, D., Levy, S., Levy, R., 1999. Rapid production of specific vaccines for lymphoma by expression of the tumor-derived single-chain Fv epitopes in tobacco plants. Proc. Natl. Acad. Sci. USA 96, 703-708.
Pappu, H.R., Karasev, A.V., Anderson, E.J., Pappu, S.S., Hilf, M.E., Febres, V.J., Eckloff, R.M.G., McCaffery, M., Boyko,V., Gowda, S., Dolia, V.V., Koonin, E.V., Gumpf, D.J., Cline, K.C., Garnsey, S.M., Dawson, W.O., Lee, R.F., Niblett, C.L., 1994. Nucleotide sequence and organization of eight 3' open reading frames of the *Citrus tristeza closterovirus* genome. Virology 199, 35-46.
Peremyslov, V.V., Hagiwara Y., Dolja, V.V., 1999. HSP70 homolog functions in cell-to-cell movement of a plant virus. Proc. Natl. Acad. Sci. USA 96, 14771-14776.
Pogue,G.P., Lindbo, J.A., Garger, S.J., Fitzmaurice, W.P., 2002. Making an ally from an enemy: plant virology and the new agriculture. Annu. Rev. Phytopathol. 40, 45-74.
Prasher, D.C., Eckenrode, V.K., Ward, W.W., Prendergast, F.G., Cormier, M.J., 1992. Primary structure of the *Aequorea victoria* green-fluorescent protein. Gene 111, 229-233.
Rabindran, S., Dawson, W.O., 2001. Assessment of recombinants that arise from the use of a TMV-based transient expression vector. Virology 284, 182-189.
Raju, R., Huang, H.V., 1991. Analysis of *Sindbis virus* promoter recognition in vivo, using novel vectors with two subgenomic mRNA promoters. J.Virol. 65, 2501-2510.
Robertson, C.J., Garnsey, S.M., Satyanarayana, T., Folimonova, S., Dawson, W.O., 2005. Efficient infection of *Citrus* plants with different cloned constructs of *Citrus tristeza virus* amplified in *Nicotiana benthamiana* protoplasts. Proc. $16^{th}$ Conf. IOCV, 187-195. IOCV, Riverside, CA.
Rommens, C.M., Salmeron, J.M., Baulcombe, D.C., Staskawicz, B.J., 1995. Use of a gene expression system based on *Potato virus X* to rapidly identify and characterize a tomato Pto homolog that controls fenthion sensitivity. Plant Cell 7, 249-257.
Ryan, M.D., King, A.M.Q., Thomas, G.P., 1991. Cleavage of *Foot-and-mouth disease virus* polyprotein is mediated by residues located within a 19 amino acid sequence. J. Gen. Virol. 72, 2727-2732.
Ryan, M.D., Drew, J., 1994. *Foot-and-mouth disease virus* 2A oligopeptide mediated cleavage of an artificial polyprotein. EMBO J.13, 928-933.
Sablowski, R.W., Baulcombe, D.C., Bevan, M., 1995. Expression of a flower-specific Myb protein in leaf cells using a viral vector causes ectopic activation of a target promoter. Proc. Natl. Acad. Sci. USA 92, 6901-6905.
Satyanarayana, T., Gowda, S., Boyko, V.P., Albiach-Martí, M.R., Mawassi, M., Navas-Castillo, J., Karasev, A.V., Dolja, V., Hilf, M.E., Lewandowski, D.J., Moreno, P., Bar-Joseph, M., Gamsey, S.M., Dawson, W.O., 1999. An engineered closterovirus RNA replicon and analysis of heterologous terminal sequences for replication. Proc. Natl. Acad. Sci. USA 96, 7433-7438.
Satyanarayana, T., Gowda, S., Mawassi, M., Albiach-Martí, M.R., Ayllón, M.A., Robertson, C., Garnsey, S.M., Dawson, W.O., 2000.

(56) References Cited

OTHER PUBLICATIONS

Closterovirus encoded HSP70 homolog and p61 in addition to both coat proteins function in efficient virion assembly. Virology 278, 253-265.

Satyanarayana, T., Bar-Joseph, M., Mawassi, M., Albiach-Martí, M.R., Ayllón, M.A., Gowda, S., Hilf, M.E., Moreno, P., Garnsey, S.M., Dawson, W.O., 2001. Amplification of *Citrus tristeza virus* from a cDNA clone and infection of *Citrus* trees. Virology 280, 87-96.

Satyanarayana, T., Gowda, S., Ayllón, M.A., Albiach-Martí, M.R., Rabindran, S., Dawson, W.O., 2002. The p23 protein of *Citrus tristeza virus* controls asymmetrical RNA accumulation. J. Virol. 76, 473-483.

Satyanarayana, T., Gowda, S., Ayllón, M.A., Dawson, W.O., 2003. Frameshift mutations in infectious cDNA clones of *Citrus tristeza virus*: a strategy to minimize the toxicity of viral sequences to *Escherichia coli*. Virology 313, 481-491.

Scholthof, H.B., 1999. Rapid delivery of foreign genes into plants by direct rub-inoculation with intact plasmid DNA of a *Tomato bushy stunt virus* gene vector. J. Virol. 73, 7823-7829.

Folimonov, Alexey S.,. Folimonova, Svetlana Y., Bar-Joseph, Moshe, Dawson, William O. 2007, A stable RNA virus-based vector for *Citrus* trees, Virology 368, 205-216.

Shivprasad, S., Pogue, G.P., Lewandowski, D.J., Hidalgo, J., Donson, J., Grill, L.K., Dawson, W.O., 1999. Heterologous sequences greatly affect foreign gene expression in *Tobacco mosaic virus*-based vectors. Virology 255, 312-323.

Van Vloten-Doting, L., Bol, J.F., Cornelissen, B., 1985. Plant virus-based vectors for gene transfer will be of limited use because of the high error frequency during viral RNA synthesis. Plant Mol. Biol. 4, 323-326.

* cited by examiner

VIRAL-BASED TRANSIENT-EXPRESSION VECTOR SYSTEM FOR TREES

BACKGROUND

Virus-based transient-expression vectors are routine tools used in plant molecular biology laboratories throughout the world for rapidly expressing or silencing genes in plants. They also can be important tools in plant genomics to screen unknown sequences for function. Yet, available vectors have been developed from a limited number of rather similar viruses of herbaceous plants. Notable examples are the vectors based on Tobacco mosaic virus (TMV) (Dawson et al., 1989; Donson et al., 1991; Shivprasad et al., 1999; Rabindran and Dawson, 2001). Tree crops offer special challenges. Even if existing vectors could infect trees, the time required for systemic infection and analysis of the expressed genes in trees generally exceeds the stability of known virus-based vectors. Yet, the challenges of breeding restraints and the decades required for improving trees greatly increase the need for useful virus-based vectors.

Citrus tristeza virus (CTV) is a member of the complex Closteroviridae family that contains viruses with mono-, bi-, and tripartite genomes transmitted by a range of insect vectors including aphids, whiteflies, and mealybugs (Bar-Joseph et al., 1979; Dolja et al., 1994; Agranovsky, 1996; Karasev, 2000). The long flexuous virions (2000 nm×10-12 nm) of CTV are encapsidated by two coat proteins: the major coat protein (CP) covering about 97% of the virion and the minor coat protein (CPm) completing encapsidation of the other terminus. The single-stranded RNA genome of CTV is approximately 19.3 kb, divided into twelve open reading frames (ORFs) (Pappu et al., 1994; Karasev et al., 1995) (FIG. 1). ORF 1*a* encodes a 349 kDa polyprotein containing two papain-like protease domains plus methyltransferase-like and helicase-like domains. Translation of the polyprotein is thought to occasionally continue through the polymerase-like domain (ORF 1*b*) by a +1 frameshift. ORFs 1*a* and 1*b* plus the nontranslated termini are all that is required for replication in protoplasts (Satyanarayana et al., 1999). Ten 3' ORFs are expressed by 3' co-terminal subgenomic (sg) mRNAs (Hilf et al., 1995; Karasev et al., 1997). In addition to the two coat proteins, p65 (HSP70 homolog) and p61 are required for efficient virion assembly, and are necessary for passage of the virus from protoplast to protoplast in order to amplify inoculum for infection of citrus trees (Satyanarayana et al., 2000). The p6 protein is needed for infection of plants as are the p20 and p23 proteins, which along with CP, are suppressors of RNA silencing (Lu et al., 2004). Remarkably, citrus trees can be infected with mutants with three genes deleted: p33, p18, and p13 (*T. Satyanarayana,* unpublished data).

The major lesson that has been learned so far from virus-based vector design is that building an effective vector requires understanding of the regulation of viral gene expression (Shivprasad et al., 1999). It is fairly easy to insert a reporter gene into your favorite virus and monitor expression in protoplasts, or for a limited time in portions of an herbaceous plant. It is much more difficult to create a vector that both expresses the inserted gene at a sufficient level and is stable long enough to be useful.

DETAILED DESCRIPTION

Figure 1:
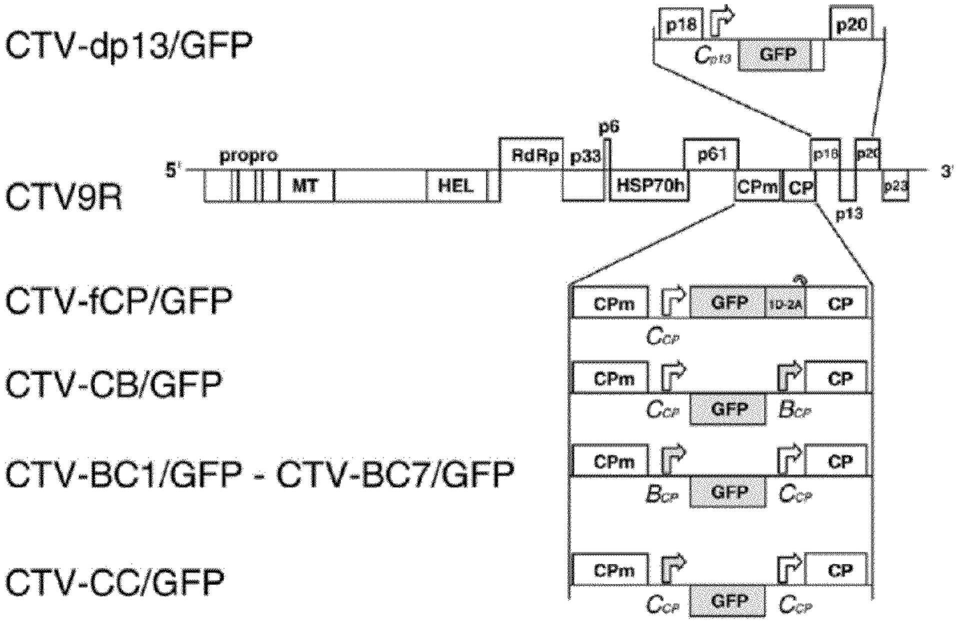
FIG. 1. Schematic diagram of the genome organization of the wild type CTV (CTV9R) and its derivatives encoding GFP. The open boxes represent ORFs and their translation products. PRO, papain-like protease domain; MT, methyltransferase; HEL, helicase; RdRp, RNA-dependent RNA polymerase; HSP70h, HSP70 homolog (p65); CPm, minor coat protein; CP, major coat protein; GFP, green fluorescent protein; 1D-2A, 1D-2A encoding sequence from Foot-and-mouth disease virus (FMDV). Round arrow indicates position of the processing site of fusion protein GFP-1D-2A-CP. Bent arrows indicate positions of BYV (Bcp), CTV CP (CcP), or CTV p13 ($C_{p13}$) sgRNA controller elements. Inserted elements are shown in grey.

The present invention is based on the inventors' work regarding several strategies for utilizing CTV as a basis for constructing a transient-expression vector for citrus trees. According to one embodiment, the invention relates to a method of transfecting a woody tree with a gene of interest. In a specific embodiment, the method enables the transfection of woody trees under field conditions to express beneficial proteins. The method includes the step of innoculating a woody tree with a CTV vector engineered to comprise said gene of interest. The gene of interest has a 5' end and a 3' end. Positioned upstream of the 5' end is an additional sgRNA control element (CE). Innoculation of the tree results in a systemic infection of the woody tree such that a majority of the virus population of the systemic infection comprises the CTV vector. Also, the CTV vector is stable enough to enable expression of the gene of interest for at least two months. Inoculation may occur by convention methods in the art. In one embodiment, inoculation occurs by grafting a portion of tissue infected with CTV vector to another tree.

The inventors have recognized that it is desired to sufficiently form virions such that the inoculum can be amplified by protoplast passage for inoculation of trees. Because of limitations of working with a viruses in woody plants, the requirements for a transient-expression vector are much more rigorous than the short term experiments possible with herbaceous plants. Not only should the levels of expression of the foreign gene be sufficiently high, but the resulting construct must be stable enough for systemic infection of trees and analysis of the foreign gene's effect on the tree. The time required is months to years. The inventors describe herein the results of different types of virus-based transient-expression vectors using CTV, and a demonstration of an ‘add-a-gene’ construct that is unusually stable. The vectors of the present invention are capable of producing copious quantities of a foreign protein for several years. The vectors are remarkably useful at equipping trees in the field with the ability to protect themselves or cure themselves of diseases.

The CTV produces ten 3'-coterminal sgRNAs that function as mRNAs for the ten 3' genes (Hilf et al., 1995), with only the 5'-most ORF of each thought to be translated. There appear to be general rules that determine the levels of production of these sgRNAs. First, genes located nearer the 3' terminus are usually expressed at higher levels. The two 3' most genes, p23 and p20, have the highest levels of sgRNAs. Also, when genes are moved closer to the 3' terminus, expression levels increase. Positioning the low expressed p33 gene near the 3' terminus results in a level of expression comparable to the highest expressed genes (p20 and p23) (Satyanarayana et al., 1999). However, there are exceptions. The CP gene, located at position 5 from the 3' end, is expressed higher than the p13 and p18 genes, located at positions 3 and 4. The second rule is that ORFs with an upstream nontranslated region are generally expressed higher than ORFs that overlap with the preceding ORF. The p23, p20, p13, CP, p6, and p33 ORFs have upstream nontranslated sequences (Pappu et al., 1994). With the exception of the 5'-most genes (p33 and p6), these are the more highly expressed genes.

The cis-acting sequences that regulate the expression of the 3' genes generally are located immediately upstream of their ORFs. We refer to these sequences as ‘controller elements’ (CE) instead of ‘promoters’ because we have not been able to determine whether the mode of production of the 3' sg mRNAs is by promotion from an internal sequence of the minus strand or termination during minus strand synthesis followed by amplification of positive-stranded sg mRNAs (Gowda et al., 2001). Each 3' CE produces two sgRNAs in addition to the expected 3'-terminal positive-stranded MRNA: a negative-stranded sgRNA with sequence complementary to the sg mRNA, and a positive-stranded 5'-terminal sgRNA that apparently terminates prematurely near the CE during genomic RNA synthesis. The 3' CEs generally consist of one or two stem-loop structures with a downstream (plus sense) +1 site corresponding to the 5' terminal adenosine of the mRNA (Gowda et al., 2001; Ayllón et al., 2005). Mutational analysis and characterization of the context of the +1 site of the sg mRNAs showed opportunities for manipulation of levels of expression several fold up or down (Ayllón et al., 2003).

In a specific embodiment, the invention pertains to a CTV vector engineered to comprise and express gene of interest, said gene of interest having a 5' end and a 3' end; and an additional sgRNA CE positioned upstream of the 5' end of said gene of interest. In a more specific embodiment, the heterologous sgRNA CE is BYV CP sgRNA CE. In an alternative embodiment, the sgRNA is an added homologous CTV CPsgRNA CE.

In an alternative method embodiment, the invention pertains to a method of producing a tree expressing a gene of interest. The method includes transfecting a first tree with a CTV vector engineered to comprise said gene of interest, said gene of interest having a 5' end and a 3' end; and a heterologous sgRNA CE positioned upstream of the 5' end of said gene of interest. A portion of the first tree is then grafted to a portion of a second tree.

EXAMPLES

Example 1

ORF Substitution Vector

The earliest prototype plant virus-based vectors were gene-substitution vectors, in which a viral ORF not necessary for replication was substituted by a foreign gene ORF. However, since the coat protein gene was the expendable gene, this version of vector failed to move or only moved poorly in intact plants (French et al., 1986; Takamatsu et al., 1987; Dawson et al., 1988; Chapman et al., 1992; Scholthof, 1999). In contrast, CTV has three genes that can be deleted with continued efficient replication and movement of the virus in citrus trees—p33, p18, and p13 (T. Satyanarayana, unpublished data). Although the p33 and p18 genes are expressed at relatively low levels, the p13 gene is expressed at moderate levels. Thus, the inventors chose to replace most of p13 ORF with the ORF of GFP, resulting in vector construct CTV-dp13/GFP (FIG. 1). In order to preserve the p20 CE that overlaps the p13 ORF, the last 21 nucleotides from the 3' end of p13 ORF were fused to the 3' end of the inserted ORF.

Figure 2:
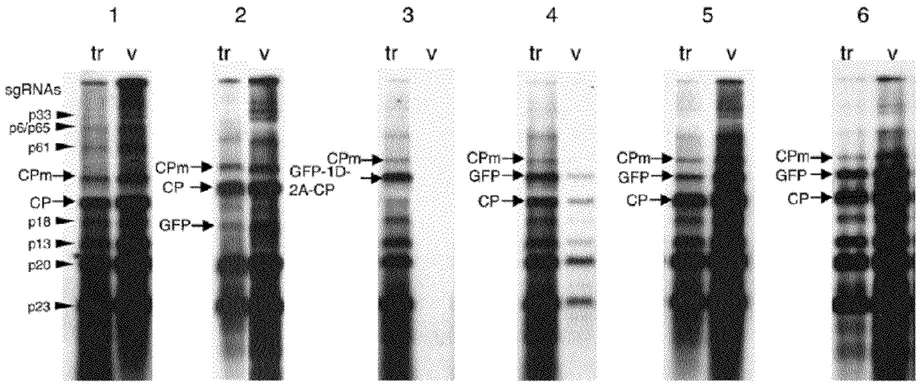
FIG. 2. Replication of CTV9R (1), CTV-dp13/GFP(2), CTV-fCP/GFP (3), CTV-CB/GFP (4), CTV-BC1/GFP (5), or CTV-CC/GFP (6) in *N. benthamiana* mesophyll protoplasts inoculated with in vitro transcripts (tr) or progeny virions (v) extracted in crude sap from initially inoculated protoplasts during subsequent passage. Total RNA was isolated from protoplasts 4 days post inoculation (dpi). Northern blot hybridizations were carried out using CTV 3' positive RNA strand-specific riboprobe. Positions of CPm, CP, GFP, and other sgRNAs are shown.

The in vitro generated RNA transcripts of pCTV-dp13/GFP were used to inoculate *Nicotiana benthamiana* protoplasts. CTV-dp13/GFP replicated well, producing normal amounts of genomic and sgRNAs as demonstrated by Northern blot hybridization analysis (FIG. 2, lane 2tr). The p13 ORF substitution did not affect the ratio of the other sgRNAs.

The ability of this vector prototype to form virions was assessed via passaging of progeny virions that were extracted from the transcript-inoculated protoplasts to a next set of protoplasts (Satyanarayana et al., 2001). CTV-dp13/GFP was passaged efficiently through a sequential series of protoplasts, with the number of protoplasts infected and the yield of virus amplified to high levels, demonstrating the facility to form good virions (FIG. 2, lane 2v).

Example 2

ORF Fusion Vector

The inventors previously examined the production of some CTV proteins fused to GFP during replication in protoplasts. A viral construct with a fusion of GFP to the C-terminus of p20 produced copious amounts of the fusion protein that fluoresced brightly and accumulated in the amorphous inclusion bodies, which represent a characteristic feature of the CTV infection (Gowda et al., 2000). Similarly, a construct with GFP fused to the C-terminus of p23 produced large amounts of the fluorescing fusion protein (T. Satyanarayana, unpublished data). Both constructs replicated normally, with little effect on regulation of the other genes, and could be passaged efficiently from protoplast to protoplast. Yet, neither construct infected plants, apparently because the fused viral protein was not functional in plants. Here it was chosen to produce similar constructs, but to 'cleave' the fusion protein and provide a functional viral protein. Because CP is one of the highest expressed proteins, we chose to examine fusions to CP. One approach is to use the 2A peptide of the Foot-and-mouth disease virus (FMDV) that mediates processing of the FMDV polyprotein by disrupting translation, which results in production of two polypeptides (Ryan et al., 1991; Donnelly et al., 2001b). The 'cleavage' occurs between the carboxy-terminal glycine residue of the 2A peptide and the amino-terminal proline residue of the 2B protein of FMDV. Insertion of the FMDV 2A region followed by a proline residue in a synthetic polyprotein has been previously shown to mediate a 'cleavage' of the polyprotein with an efficiency estimated at ~85% (Ryan and Drew, 1994). N-terminal extension of the 2A region by 14 amino acid residues from the C-terminus of the FMDV 1D protein located immediately upstream of 2A improves the 'cleavage' activity to ~99% (Donnelly et al., 2001a). Thus, in CTV-fCP/GFP a sequence encoding the polypeptide comprising 14 amino acid residues of the ID region followed by 18 amino acid residues of the 2A protein plus an additional proline codon were fused between the last codon of the GFP ORF and the first codon of the CP ORF. The expression of the fused ORF was directed by the CP sgRNA CE (FIG. 1). Translation of the gfp-1d-2a-cp gene was expected to result in accumulation of GFP-1D-2A and CP (with an additional proline at the N-terminus), with a small portion of uncleaved GFP-1D-2A-CP fusion protein.

Upon inoculation of protoplasts with in vitro synthesized transcripts of pCTV-fCP/GFP, a larger sgRNA corresponding to the expected size of the GFP-ID-2A-CP mRNA was produced, which did not affect the levels of accumulation of the other sgRNAs (FIG. 2, lane 3tr). Infected protoplasts, ~0.1% of the total number of protoplasts as expected (Satyanarayana et al., 2001), exhibited bright GFP fluorescence that was detected by observation of the protoplasts with a fluorescent microscope (data not shown). The virus was amplified by successive passage in protoplasts (FIG. 2, lane 3v).

Example 3

Add-a-Gene Vector

'add-a-gene' vectors based on TMV that produced an extra sgRNA and a foreign protein have been previously produced (Dawson et al., 1989; Donson et al., 1991; Shivprasad et al., 1999). With CTV, mini-replicon constructs were created with the GFP ORF expressed from a sg mRNA and examined its production in protoplasts, demonstrating the feasibility of expressing foreign ORFs with CTV CEs (Satyanarayana et al., 2003). However, these CTV constructs were missing most of the 3' genes and could not infect trees. Since an objective of this work was to construct a vector that would express foreign genes in citrus trees, constructs containing all of the genes required for passage and infection of plants were needed. A first question was, where to position an extra gene for stable and high-level expression? The inventors chose to insert the foreign ORF between the CP and CPm genes because the CP sgRNA CE was defined better than other CEs (Gowda et al., 2001; Ayllón et al., 2004). A next question was, what to use as a CE for the foreign ORF? With TMV, insertion of homologous sequence repeats caused vector constructs to be unstable (Dawson et al., 1989), but heterologous repeats using a promoter sequence from a related virus were relatively stable (Donson et al., 1991). Based on the TMV results, Peremyslov et al. (1999) created a vector from the closterovirus Beet yellows virus (BYV) using an extra heterologous CE from Beet yellow stunt virus.

A set of three 'add-a-gene' constructs with an additional CE were examined (FIG. 1). Vector construct CTV-CC/GFP had a homologous duplication of CTV CP sgRNA CE controlling expression of both GFP and CP ORFs. An upstream sequence thought to contain the heterologous CP sgRNA CE of BYV was inserted into constructs CTV-CB/GFP and CTV-BC1/GFP. CTV-CB/GFP was designed so that the native CP sgRNA CE would control the GFP ORF while the heterologous BYV CP sgRNA CE would control the CP ORF. CTV-BC1/GFP was designed such that the CTV CP ORF would be controlled by its native CE, and the GFP ORF would be controlled by the heterologous CE.

Figure 3:
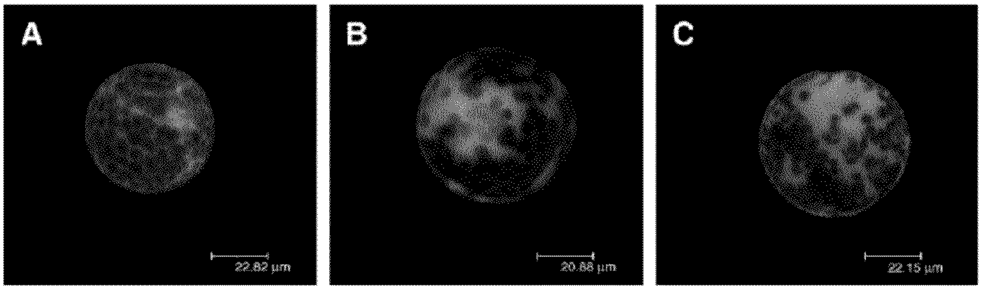
FIG. 3. Confocal laser scanning microscope images of protoplasts of *N. benthamiana* infected with (A) TMV-30BGFP (Shivprasad et al, 1999), (B) CTV-BC1/GFP, (C) CTV-CC/GFP. Images were taken at 4 dpi.

Inoculation of protoplasts with transcripts derived from cDNAs of each of these constructs resulted in efficient replication of the vectors (FIG. 2). Northern hybridization blots of each construct showed an extra sgRNA between the CPm and CP sgRNAs, with the larger sgRNAs shifted upward. The levels of the viral sgRNAs appeared to be unaffected by the production of the extra sgRNA. However, the sgRNAs controlled by the heterologous BYV sgRNA CE were reduced compared to those controlled by the native CP sgRNA CE: that of CP in CTV-CB/GFP and GFP in CTV-BC1/GFP (FIG. 2, lanes 4tr and Str). The levels of both sgRNAs were high in CTV-CC/GFP (FIG. 2, lane 6tr). Production of GFP was confirmed for all three constructs by observation of fluorescence with a UV-fluorescence microscope. In order to estimate the level of production of the foreign protein by the CTV-based vectors, we compared levels of accumulation of GFP per protoplast to that produced by the TMV-based vector (Shivprasad et al., 1999) in the same set of protoplasts. FIG. 3 shows that the levels of fluorescence of individual protoplasts infected with each of the constructs were high and similar to that of protoplasts infected with TMV-30B GFP.

The ability of these vectors to be passaged in protoplasts was examined as described above.

Similar to the parental wild type virus (FIG. 2, lane 1v), CTV-BC1/GFP and CTV-CC/GFP passaged efficiently, resulting in significant increases in infectivity in subsequent passages, which was detected as an increase in number of GFP fluorescent protoplasts (data not shown) and in greater accumulation of the genomic and sgRNAs (FIG. 2, lanes 5v and 6v), thus indicating the ability of these constructs to form viable virions. However, CTV-CB/GFP exhibited dramatically decreased levels of accumulation of RNA after the first passage compared to the initial transcript inoculation (FIG. 2, lane 4v), and failed to be passaged further. The inability to be passaged was correlated with the reduced production of CP sgRNA, which apparently resulted in insufficient virion formation. Since CTV-CB/GFP could not be amplified by passage for infection of citrus trees, it was not used in further experiments.

Example 4

Effects of Length of Heterologous CE

Figure 4:
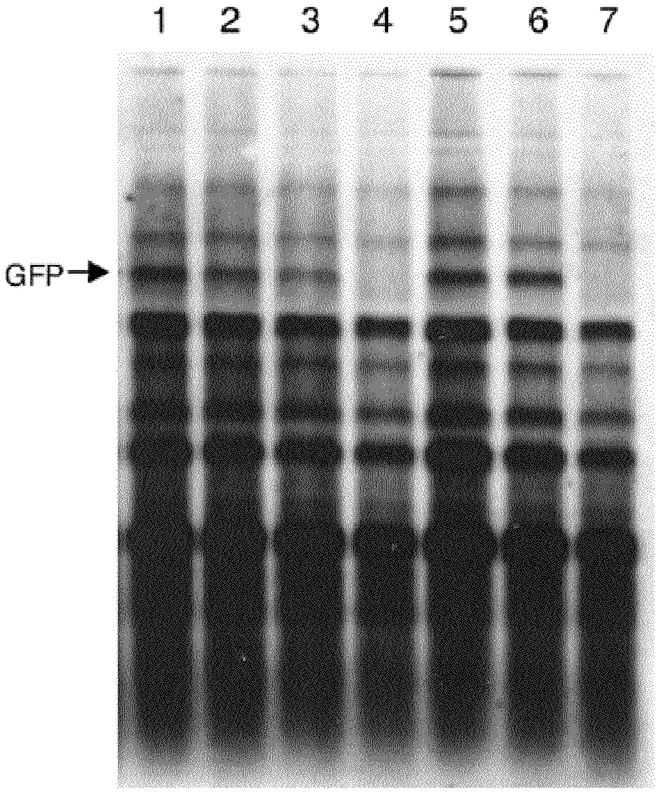
FIG. 4. Northern blot analysis of total RNA isolated from *N. benthamiana* protoplasts inoculated with transcripts of pCTV-BC1/GFP (1), pCTV-BC2/GFP (2), pCTV-BC3/GFP (3), pCTV-BC4/GFP (4), pCTV-BC5/GFP (5), pCTV-BC6/GFP (6), or pCTV-BC7/GFP (7) at 4 dpi. The blot was hybridized with positive-stranded RNA - specific probe. Position of GFP sgRNA is shown.

The BYV sgRNA CE has not been characterized. Thus, an arbitrary length of sequence upstream of the BYV CP ORF for CTV-BC1/GFP was chosen. To examine the effect of different lengths of this upstream sequence, a series of six vector constructs were built based on CTV-BC1/GFP with progressively shorter fragments inserted in front of the GFP ORF (Table 1). These constructs were analyzed for levels of accumulation of the GFP sg mRNA (FIG. 4) and levels of GFP fluorescence in protoplasts. Compared to CTV-BC1/GFP (FIG. 4, lane 1), the truncation of the BYV sgRNA CE to 125 nts in CTV-BC2/GFP resulted in a slightly reduced level of accumulation of the GFP sgRNA (FIG. 4, lane 2). CTV-BC3/GFP (113 nts) and especially CTV-BC4/GFP (101 nts) exhibited even greater reductions of the sgRNA (FIG. 4, lanes 3, 4). Interestingly, the further truncation of the CE to 89 nts in CTV-BC5/GFP and to 77 nts in CTV-BC6/GFP resulted in increased levels of the sgRNA accumulation to that of equal or greater than that of CTV-BC1/GFP (FIG. 4, lanes 5, 6 and lane 1). However, the truncation of 12 additional nts of the BYV sgRNA CE in CTV-BC7/GFP completely abolished accumulation of the GFP sg mRNA (FIG. 4, lane 7). The levels of GFP fluorescence observed in protoplasts inoculated with these constructs always correlated with the amounts of GFP sg mRNA: bright fluorescence in protoplasts infected with CTV-BC1/GFP, CTV-BC2/GFP, CTV-BC5/GFP, and CTV-BC6/GFP; weak fluorescence in protoplasts inoculated with CTV-BC3/GFP; and no GFP fluorescence in protoplasts infected with CTV-BC4/GFP or CTV-BC7/GFP (data not shown).

Example 5

Figure 5:
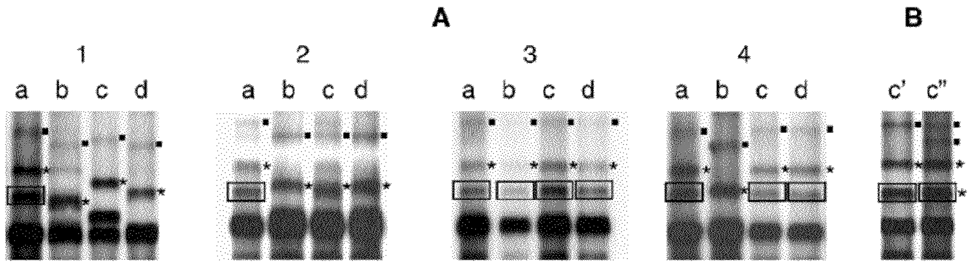
FIG. 5. (A) Northern blot analysis of total RNA isolated from *N. benthamiana* protoplasts inoculated with passaged virions (a) or virions extracted from *Citrus macrophylla* seedlings (b,c,d) infected with CTV-based vector constructs. Lanes b, c, and d represent three individual plants used for initial inoculation with vector constructs. Seedlings were infected for 12 months with CTV-CC/GFP (1), CTV-BC1/GFP (2), CTV-BC5/GFP (3) or for 24 months with CTV-BC5/GFP (4). It should be noted that the wild type CPm sgRNA and the GFP sgRNA run at approximately the same position; thus, loss of the GFP ORF in a vector construct is evidenced by the shift downward of the higher sgRNAs (i.e. p61 and CPm sgRNAs). Lanes b,c, and d in 1 and 2 and lane 4b demonstrate evidence of the GFP gene loss. (B) Northern blot comparison of patterns of sgRNAs accumulated in protoplasts transfected with virus progeny produced upon propagation of CTV-BC5/GFP infection from initially inoculated plant (represented here, lane 4c) into ten new *C. macrophylla* seedlings. Lanes c' and c" represent two out of ten inoculated plants. c" represents a plant with a mixed population of an intact vector and a wild-type-like recombinant. This is evident by the presence of the vector-specific p61 sgRNA and the appearance of a shorter wild-type-like p61 sgRNA. sgRNAs corresponding to the intact GFP ORFs are shown in boxes. Positions of sgRNAs for p61 and CPm are designated with bold dot or star, respectively.

Stability of the Inserted Sequences in the Vectors During Extended Passage in Protoplasts Vectors with the highest levels of GFP expression, CTV-BC1/GFP, CTV-BC5/GFP, and CTV-CC/GFP, were examined during a series of eleven sequential passages in protoplasts (which represented 44 days of replication) for their stability. The patterns of sgRNAs remained unchanged during these passages for all three vector constructs (FIG. 5A, lanes 1a, 2a,3a). No additional bands resulting from the deletion of the foreign sequence inserted were detected, even with overexposure of the blots; thus, showing similar genetic stability of the constructs during replication in protoplasts.

Example 6

Expression of GFP in Citrus Trees

Figure 6:
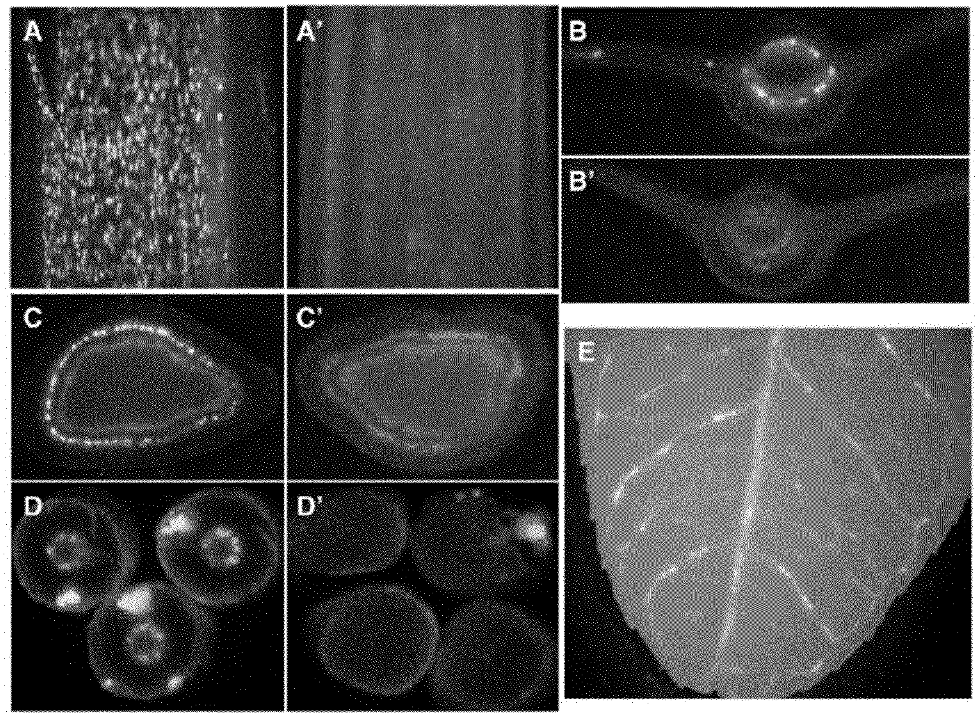
FIG. 6. Detection of GFP fluorescence in phloem-associated cells of *C. macrophylla* plants infected with GFP-expressing CTV-BC1/GFP at 5 weeks after inoculation (A-E). A'-D', control C. macrophylla plants infected with wild type CTV. A and A', internal surface of the young bark; B and B', cross-section through young petioles; C and C', cross-section through young stems; D and D', cross-section through young roots; E, abaxial side of young leaf.

After the above series of passages in protoplasts, progeny virions were concentrated via sucrose cushion centrifugation and used for inoculation of citrus trees (Robertson et al., 2005). At five weeks after inoculation, GFP-expressing vectors were found to have replicated and moved systemically in the young trees as demonstrated by ELISA using CTV-specific antiserum (data not presented) and by observation of GFP fluorescence (FIG. 6). The symptom phenotype of the trees infected with the vector constructs was similar to that of trees infected with the parental wild type virus. Infected plants developed veinal chlorosis and mild epinasty in young leaves. Also, the time intervals for establishing systemic infections and symptom production in infected citrus plants were similar between the wild type CTV and CTV-based vectors.

GFP fluorescence was detected in phloem-associated cells of young, developing parts of the trees: in the bark of stems, in young leaves and petioles, and in young roots of infected seedlings (FIG. 6).

Example 7

Long-Term Stability of the Vectors in Citrus Trees

The stability of the inserted GFP gene in CTV-BC1/GFP, CTV-BC5/GFP, and CTV-CC/GFP in citrus trees was examined at different times after inoculation by analyzing the pattern of sgRNAs and by monitoring GFP expression in the growing areas of the trees. Since the infected cells in the tree are at different stages of replication, it is difficult to get good sgRNA profiles from RNA extracted directly from the trees. To avoid this complication, virions were extracted from growing parts of the trees and used for inoculum for protoplasts. Total RNA isolated from protoplasts 4 days after inoculation was analyzed by Northern blot hybridizations and compared to the corresponding RNA samples isolated earlier during the protoplast passaging of the vectors. At 6 weeks after inoculation of the trees, no changes in sgRNAs patterns were detected and GFP fluorescence in the trees was uniform for all of the vectors (data not shown), demonstrating that the insertions remained in all vectors.

The GFP fluorescence was further monitored in all infected trees for several months. At one year after inoculation of trees, the GFP fluorescence in plants infected with CTV-CC/GFP and CTV-BC1/GFP was still visible, but the number of fluorescent cells was reduced in some trees. The progeny virions analyzed by amplification in protoplasts showed patterns of sgRNAs that demonstrated loss of the GFP insert for both vectors in each set of three trees that were examined in this experiment. The patterns represented mixed populations of intact vector and virus in which the extra GFP sgRNA was partially or completely lost, as indicated by the downward shifts of the p61 and CPm sgRNAs (FIG. 5A, 1 and 2). Thus, the reduced GFP fluorescence still present in those plants apparently was due to the mixed population containing a minor component consisting of the original vector plus a major component consisting of a recombinant with all or part of the insert removed. Interestingly, none of the three trees infected with CTV-BC5/GFP had any evidence of loss of the GFP gene after one year. The extracted virus assayed in protoplasts showed no loss of the GFP sgRNA (FIG. 5A, 3), and GFP fluorescence was evenly distributed throughout the plants (data not shown). When viral RNAs from these plants were analyzed at two years after inoculation, loss of the GFP insert was detected only in one out of three trees (FIG. 5A, 4).

To examine the stability of CTV-BC5/GFP further, one of the plants in which the vector remained stable for two years was used as inoculum for ten new citrus trees. Analysis of the virus population six months after infection revealed that only one plant out of ten contained virus with the insertion deleted as a minor component of population, which was noted by an appearance of an additional band corresponding to the wild type p61 sgRNA on Northern hybridization blots (FIG. 5B, c' and c"). Several trees from the original inoculations in which the CTV-BC5/GFP are still stably producing GFP fluorescence after more than five years.

Example 8

Competitiveness of the CTV-Based Vector with the Wild Type Virus

To examine the competitiveness of the original vector, CTV-BC5/GFP, with the recombinants, the virus mixture isolated from the plant with the mixed population (FIG. 5B, lane c") was further propagated by inoculation of five new trees, and the progeny virus was assayed four months later. In all of these plants, the ratio of the intact vector to the recombinants did not significantly change, with the wild-type-like recombinants remaining a minor component (data not shown). These observations suggest that when a deletion to the wild-type-like virus occurs, the vector is not quickly overgrown by the wild-type-like recombinant.

Figure 7:
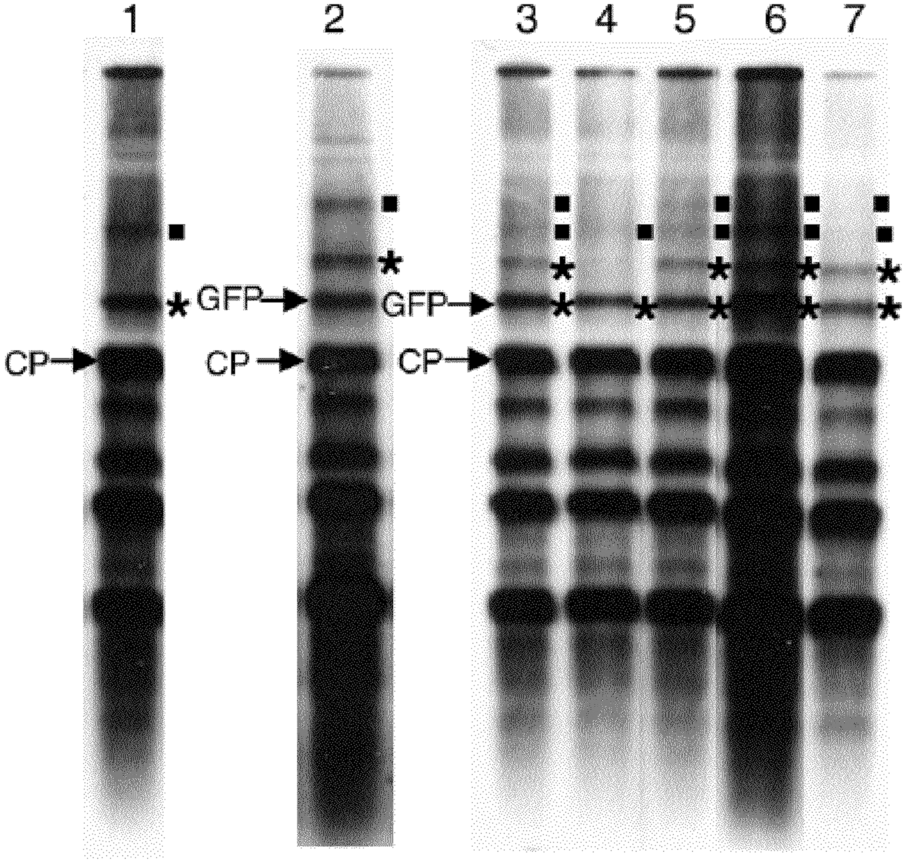
FIG. 7. Northern blot analysis of total RNA isolated from *N. benthamiana* protoplasts inoculated with virions extracted from *C. macrophylla* seedlings infected with wild type CTV9R (1), CTV-BC5/GFP (2), or CTV9R plus CTV-BC5/GFP (3, 4, 5, 6, 7). Each lane represents individual infected tree. Seedlings were infected for 4 months. Positions of CP and GFP sgRNAs are shown. Positions of sgRNAs for p61 and CPm are designated with bold dot or star, respectively. It should be noted that the wild type CPm sgRNA and the GFP sgRNA run at the approximately same position; thus, loss of the GFP ORF in a vector construct is evidenced by the shift downward of the higher sgRNAs (i.e. p61 and CPm sgRNAs). The blot was hybridized with positive-stranded RNA-specific probe.

Thus, the vector appeared to be competitive with the recombinant wild-type-like virus. To examine whether these recombinant viruses were less competitive than the wild type virus for some unknown reason, we examined the competitiveness of the vector with the wild type virus in another experiment in which five citrus trees were simultaneously inoculated with two viruses—wild type CTV and CTV-BC5/GFP. After two months and four months of infection, the virus populations in the flush of new growth at the top of the trees were analyzed. The resulting virus in the new growth was a mixture of both viruses (FIG. 7), demonstrating that the vector was not overgrown by the wild type virus. Thus, one component of the stability of the CTV-based vector is its ability to compete with the recombinant wild-type-like virus.

Example 9

Significance and Analysis of Examples 1-8

The 'add-a-gene' vectors worked best of the strategies that that were examined. Insertion of the foreign gene between the two coat proteins genes was examined. Of the constructs examined, the choice and place of CEs greatly affected their effectiveness. The heterologous CE from BYV when used to control CP expression in CTV-CB/GFP resulted in too little CP for efficient passage for amplification of inoculum to infect trees. The vector using the heterologous BYV sgRNA CE to control GFP expression produced slightly less GFP MRNA, but produced sufficient amounts of CP from the native CE to allow efficient passage and amplification. Remarkably, the size of the heterologous BYV sgRNA CE substantially affected the levels of the GFP mRNA. There was no clear relationship between size and strength of the CE. As the inserted sequences were shortened, the levels of mRNA decreased, increased, and decreased again, suggesting that structural interactions that affect the function of the CE were altered upon changing the lengths of sequences. The differences were great enough to justify empirically testing different lengths of sequence for optimal expression.

From observations of several different CTV constructs, it appears that the level of CP produced cannot be reduced much below the wild type level without reducing the yield of virions.

Previous work that examined expression of an extra gene in TMV clearly demonstrated that there was competition between the different sgRNAs—increases in one sgRNA resulted in decreases in others (Shivprasad et al., 1999). Additionally, manipulation of the sgRNA promoters within wild type TMV similarly changed the ratio of the 30K and CP sgRNAs (Grdzelishvili et al., 2000). In designing a TMV-based vector, production of the sgRNA for the extra (inserted) gene occurred at the expense of the sgRNAs of the native genes (30K and CP). Thus, with TMV, the optimal vector resulted from a compromise between reduced levels of CP and movement protein that were still sufficient for virion assembly and movement and a corresponding increase in production of the foreign protein (Shivprasad et al., 1999). Similar competition in production of viral sgRNAs has been shown with Barley stripe mosaic virus (Johnson et al., 2003) and Sindbis virus (Raju and Huang, 1991). In contrast, there appears to be no competition in production of the different sg mRNAs by CTV. Inserting a new gene or increasing or decreasing the levels of expression of different genes had little or no effect on the levels of sg mRNA production by the other genes (Ayllón et al., 2003).

CTV appears to differ from alpha-like RNA viruses in production of sg mRNAs. It is not yet certain whether closteroviruses produce sg mRNAs by initiation from a promoter on the negative strand like alpha-like RNA viruses, or by terminating negative strand synthesis at the CE and using that minus-stranded sgRNA as a template for the mRNAs (Gowda et al., 2001). However, the production of sg mRNAs by CTV clearly differed from that of alpha-like RNA viruses in that the '+1 nt' tolerated considerable modification (Ayllón et al., 2003; 2004). Another unusual characteristic of CTV is that the p23 gene controls the ratio of plus to minus strands of the sgRNAs (Satyanarayana et al., 2002). The lack of competition of sgRNAs is another line of evidence suggesting that the mechanisms of production of sg mRNAs by closteroviruses differ from those of alpha-like RNA viruses.

A major advantage of virus-based vectors is a high level of expression, and, thus, high-titer viruses like TMV and Potato virus X (PVX) (Chapman et al., 1992) were utilized first. Although CTV is more limited in tissue tropism than these viruses, the levels of foreign gene production per infected protoplast by the CTV-based vectors were similar to that of TMV. A major limitation of virus-based vectors has been their lack of stability. For example, the vectors that are used most widely as laboratory tools are those based on TMV and PVX, but their progeny populations are overcome by recombinants that have lost most of the inserted sequences during the systemic infection of their hosts within a couple of weeks. In contrast, CTV-based vectors have remained the major component of the population for as long as five years. Without being bound to any theory, the inventors expect that eventually the vector will be overtaken by recombinants. Even though the vector can compete with the wild type virus for years, it is likely that the wild type virus will have a competitive advantage in the long term. It should be noted that the construct CTV-BC1/GFP did not appear as stable as CTV-BC5/GFP. Other CTV-BC1 constructs with different foreign genes that appear to be as stable as CTV-BC5/GFP. Thus, other factors such as errors incorporated during cloning and propagation of the cDNA or founder effects during the movement and systemic infection of trees might determine which vectors last longer.

Instability generally has been blamed on high error rates of RNA virus replication and high rates of recombination. In fact, the error rate of RNA viruses at one time was thought to be so high that it was argued that it would be impossible to utilize RNA viruses as transient-expression vectors (Van Vloten-Doting et al., 1985). Yet, the sequence of CTV appears to be unusually stable. The inventors have discovered that the sequences of different isolates of CTV maintained in different countries and in different varieties of citrus for more than a hundred years were essentially identical (Albiach-Marti et al., 2000). However, recombination of CTV appears not to be limited. Most wild populations contain multiple defective RNAs that apparently resulted from facile recombination (Mawassi et al., 1995). For TMV-based vectors, it was shown that repeated sequences decreased stability, apparently by increasing recombination rates (Dawson et al., 1989; Donson et al., 1991). This instability could be partially overcome by using promoters from different tobamoviruses instead of repeated promoters (Donson et al., 1991; Rabindran and Dawson, 2001). However, repeated sequences in the CTV-based vector resulting from duplicated CP sgRNA CEs controlling the GFP and CP genes did not appreciably decrease stability. The stability of the CTV-based vectors appears not to be due to reduced recombination, but to increased competitiveness with the potential wild-type-like recombinant. When inoculated simultaneously with the wild type virus, the CTV-based vectors with an extra gene were able to compete effectively with the wild type virus during replication and movement throughout citrus trees. In contrast, the TMV-based vectors compete poorly with the wild-type-like recombinants for both cell-to-cell and long-distance movement (Rabindran and Dawson, 2001). Thus, the TMV recombinants quickly overcome the vector during spread in the plant. Even though recombinants with the inserted sequences deleted are produced in the CTV populations, there appears to be little selection for these recombinants to be increased proportionally in the populations.

CTV is a large virus with ten 3' genes expressed through sg mRNAs. The addition of an extra gene had no obvious effect on the virus. In the experiments described herein, the vector constructs appeared to be competitive with the wild type virus.

A limitation of CTV is that it is generally limited to phloem-associated cells. Thus, the vectors described here may not be the best for expression of genes in other tissues. However, the inventors have found that this potential limitation can be reduced somewhat by producing proteins with secretion signal peptides to export the protein out of the cell into the intercellular space where the protein or peptide is dispersed in the liquid films between cells (unpublished data).

Especially in woody plants, the transient-expression vector is a valuable tool to complement stable transformation. The potyvirus, Plum pox virus, recently was used to express GFP to examine movement of the virus in susceptible and resistant stone fruit trees (Lansac et al., 2005; Ion-Nagy et al., 2006). Transformation of citrus trees can take a year to produce a 2-inch tall plant and 5 to 20 years until the effect of the transgene on mature tree characteristics can be examined. The value of the virus-based vector is that once it infects a tree, it can be easily and quickly graft-inoculated to unlimited numbers of other susceptible trees of different varieties or species or different ages, including mature trees, and the virus-based vector can express new genes in trees or remove existing gene functions by RNA silencing relatively quickly. Although CTV has expressed GFP stably for more than five years, we do not advocate using the vector for expression in the field. Instead, the vector should be used to quickly identify genes that could improve trees followed by permanent expression through genetic transformation.

Example 10

Materials and Methods Relevant to Examples 1-8

Plasmid Constructs

The full-length cDNA clone of CTV T36, pCTV9R (Satyanarayana et al., 1999; 2003), was the basis of all constructs in this study. pCTV9R was digested with SpeI and XmaI restriction endonucleases and a resulting 7.6 kb fragment (nts 11659-19293 plus the NotI site) encompassing ORFs p6 to p23 plus the 3' nontranslated region was ligated into pGEM7Z+ (Promega) between XbaI and XmaI restrictions sites to generate pGEM-3'CTV. The wild type GFP ORF (Prasher et al., 1992) was inserted into pGEM-3'CTV by overlap-extension PCR (Higuchi et al., 1988) and subdloning (see below). The full-length CTV vector constructs were produced by ligation of PmeI-NotI fragments of GFP-harboring pGEM-3'CTV derivatives into similarly digested pCTV9R.

To engineer pGEM-dp13/GFP, the sequence encoding the first 112 amino acids of the p13 ORF was replaced by the GFP ORF. The resulting ORF began with the original p13 translation start codon and encoded the complete GFP fused to seven C-terminal amino acids (SLLPCDN) of the p13 ORF. This design preserved the p20 CE that overlaps the p13 ORF. To construct pGEM-fCP/GFP, the ORF of GFP and a sequence of FMDV 1D-2A plus an additional proline codon (encoding amino acids:
GLEARHKQKIVAPVKQTLNFDLLKLAGDVESNPGP)
were incorporated into pGEM-3' CTV. pGEM-fCP/GFP possessed a modified ORF beginning with the original CP translation start codon and comprising the complete GFP ORF, the sequence encoding the 1D-2A peptide plus proline codon, followed by the CTV CP ORF.

The GFP ORF was inserted in the region between the CPm and CP genes to produce pGEM-CB/GFP, pGEM-BC1/GFP through pGEM-BC7/GFP, and pGEM-CC/GFP. Construct pGEM-CB/GFP contained an insertion of the GFP ORF followed by the sequence of CP sgRNA CE of BYV (nts 13499-13637) (Peremyslov et al., 1999) upstream of the translation start codon of the CTV CP ORF (between corresponding nts 16151 and 16152 in CTV genome). A set of constructs pGEM-BCl/GFP through pGEM-BC7/GFP contained insertions of the BYV CP sgRNA CE sequence of various lengths (Table 1), the restriction site for PacI, the GFP ORF, followed by the restriction site for XhoI downstream termination codon of the CPm ORF (between corresponding nts 16058 and 16059 in CTV sequence). The construct pGEM-BC1/GFP was used as a template for overlap-extension PCR to replace the sequence of BYV sgRNA CE with the CTV CP sgRNA CE (nts 16059-16151) to produce pGEM-CC/GFP.

PmeI—NotI fragments of pGEM-dp13/GFP, pGEM-fCP/GFP, pGEM-CB/GFP, pGEM-BC1/GFP through pGEM-BC7/GFP, and pGEM-CC/GFP were subdloned into pCTV9R digested with the same enzymes to produce full-length CTV constructs pCTV-dp13/GFP, pCTV-fCP/GFP, pCTV-CB/GFP, pCTV-BC1/GFP through pCTV-BC7/GFP, and pCTV-CC/GFP, respectively (FIG. 1). The clones were sequenced to verify the accuracy of insertions prior to further analysis.

Protoplasts Transfection, Observation of GFP Fluorescence, Northern Blot Analysis of Viral RNAs, and Passaging of Virions in Protoplasts The procedures for the isolation of mesophyll protoplasts from N. benthamiana leaves and their transfection with SP6 RNA polymerase-derived transcripts of CTV cDNAs linearized with NotI were carried out as described by Satyanarayana et al. (1999). The expression of GFP fluorescence in infected protoplasts was observed at 4 dpi with a Zeiss Stemi SV 11 UV-fluorescence dissecting microscope (Carl Zeiss Jena, GmbH., Jena, Germany) and with a confocal scanning microscope Leica TCS SL (Leica Microsystems, Inc., Exton, Pa.). Protoplasts were harvested and divided into two portions: one used for total nucleic acids isolation, and the other stored at −70° C. for subsequent protoplast passage of virions. The total RNA isolated from protoplasts at 4 dpi were analyzed by Northern blot hybridization using a 3' positive-stranded RNA-specific riboprobe (Satyanarayana et al., 1999). Passaging of virions in crude sap through up to eleven successive cycles in protoplasts for amplification of the virus and virion assembly assay were done as described previously by Satyanarayana et al. (2000).

Inoculation of Citrus Seedlings and Observation of GFP Fluorescence in Infected Plants Amplified progeny virions from the final passages in protoplasts were extracted and concentrated by sucrose cushion centrifugation, and the concentrated virions were used for mechanical inoculation of small *C. macrophylla* trees as described by Robertson et al. (2005). Double antibody sandwich indirect ELISA was performed as described previously (Garnsey and Cambra, 1991) to confirm infection in inoculated plants. Samples of leaves, stems, or roots were taken at different time points beginning at 2 weeks after inoculation of citrus trees. Transverse and longitudinal sections of plant material were prepared by hand with a razor blade. Unfixed specimens were mounted in water and GFP fluorescence was observed with the UV-fluorescence dissecting microscope with an attached camera Olympus Q-color 5 (Olympus America, Inc., Center Valley, Pa.).

Analysis of Virus Population Accumulated in Citrus Trees Infected with CTV-Based Vector Constructs To examine virus populations in citrus trees, bark of young trees infected with the CTV-based vector constructs was peeled and ground with liquid nitrogen. CTV virions were extracted with 40 mM phosphate buffer, pH 7.4 added according to the ratio: 3 ml of buffer for 0.5 g of bark tissue. Extracts were clarified at 4000 g, and 100·1 of supernatant containing virions was used for inoculation of *N. benthamiana* mesophyll protoplasts as described by Satyanarayana et al. (1999). Total RNA isolated from protoplasts at 4 dpi was analyzed by Northern blot hybridization as described above. The genetic stability of GFP-expressing constructs was evaluated by the pattern of sgRNA accumulation.

RELATED REFERENCES

The following list includes the full cites of references described above and additional related references. The disclosures of all references cited herein are incorporated in their entirety to the extent non inconsistent with the teachings herein.

Agranovsky, A. A., 1996. Principles of molecular organization, expression, and evolution of closteroviruses: over the barriers. Adv. Virus Res. 47, 119-158.

Albiach-Marti, M. R., Mawassi, M., Gowda, S., Satyanarayana, T., Hilf, M. E., Shanker, S., Almira, E. C., Vives, M. C., Lopez, C., Guerri, J., Flores, R., Moreno, P., Garnsey, S. M., Dawson, W. O., 2000. Sequences of Citrus tristeza virus separated in time and space are essentially identical. J.Virol. 74, 6856-6865.

Alzhanova, D. V., Napuli, A. J., Creamer, R., Dolja, V. V., 2001. Cell-to-cell movement and assembly of a plant closterovirus: roles for the capsid proteins and Hsp70 homolog. EMBO J. 20, 6997-7007.

Arazi, T., Lee Huang, P., Huang, P/ L., Zhang, L., Moshe Shiboleth, Y., Gal-On, A., Lee-Huang, S., 2002. Production of antiviral and antitumor proteins MAP30 and GAP31 in cucurbits using the plant virus vector ZYMV-AGII. Biochem. Biophys. Res. Commun. 292, 441-448.

Atkinson, R. G., Bieleski, L. R. F., Gleave, A. P., Janssen, B. J., Morris, B. A. M., 1998. Post-transcriptional silencing of chalcone synthase in petunia using a geminivirus-based episomal vector. Plant J. 15, 593-604.

Ayllón, M. A., Gowda, S., Satyanarayana, T., Karasev, A. V., Adkins, S., Mawassi, M., Guerri, J., Moreno, P., Dawson, W. O., 2003. Effects of modification of the transcription initiation site context on Citrus tristeza virus subgenomic RNA synthesis. J. Virol. 77, 9232-9243.

Ayllón, M. A., Gowda, S., Satyanarayana, T., Dawson, W. O., 2004. cis-acting elements at opposite ends of the Citrus tristeza virus genome differ in initiation and termination of subgenomic RNAs. Virology 322, 41-50.

Ayllón, M. A., Satyanarayana, T., Gowda, S., Dawson, W. O., 2005. An atypical 3'-controller element mediates low-level transcription of the p6 subgenomic mRNA of Citrus tristeza virus. Mol. Plant Pathol. 6, 165-176. Bar-Joseph, M., Garnsey, S. M., Gonsalves, D., 1979. The closteroviruses: a distinct group of elongated plant viruses. Adv. Virus Res. 25, 93-168.

Chapman, S., Kavanagh, T., Baulcombe, D., 1992. Potato virus Xas a vector for gene expression in plants. Plant J. 2, 549-557.

Culver, J. N., 1996. Tobamovirus cross protection using a potexvirus vector. Virology 226, 228-235.

Dawson, W. O., Bubrick, P., Grahtham, G. L., 1988. Modifications of the tobacco mosaic virus coat protein gene affecting replication, movement, and symptomatology. Phytopathology 78, 783-789.

Dawson, W. O., Lewandowski, D. J., Hilf, M. E., Bubrick, P., Raffo, A. J., Shaw, J. J., Grantham, G. L., Desjardins, P. R., 1989. A Tobacco mosaic virus-hybrid expresses and loses an added gene. Virology 172, 285-292.

Dolja, V. V., Karasev, A. V., Koonin, E. V., 1994. Molecular biology and evolution of closteroviruses: sophisticated build-up of large RNA genomes. Annu. Rev. Phytopathol. 32, 261-285.

Donnelly, M. L. L., Hughes, L. E., Luke, G., Mendoza, H., ten Dam, E., Gani, D., Ryan, M. D., 2001a. The 'cleavage' activities of Foot-and-mouth disease virus 2A site-directed mutants and naturally occurring '2A-like' sequences. J. Gen. Virol. 82, 1027-1041.

Donnelly, M. L., Luke, G., Mehrotra, A., Li, X., Hughes, L. E., Gani, D., Ryan, M. D., 2001b. Analysis of the aphthovirus 2A/2B polyprotein 'cleavage' mechanism indicates not a proteolytic reaction, but a novel translational effect: a putative ribosomal 'skip'. J. Gen. Virol. 82, 1013-1025.

Donson, J., Kearney, C. M., Hilf, M. E., Dawson, W. O., 1991. Systemic expression of a bacterial gene by a Tobacco mosaic virus-based vector. Proc. Natl. Acad. Sci. USA 88, 7204-7208.

French, R., Janda, M., Ahlquist, P., 1986. Bacterial gene inserted in an engineered RNA virus: efficient expression in monocotyledonous plant cells. Science 231, 1294-1297.

Garmsey, S. M., Cambra, M., 1991. Enzyme-linked immunosorbent assay (ELISA) for citrus pathogens. In: Roistacher, C. N. (Ed.), Graft-Transmissible Diseases of Citrus, Handbook for Detection and Diagnosis. FAO, Rome, pp. 193-216.

Gowda, S., Satyanarayana, T., Davis, C. L., Navas-Castillo, J., Albiach-Marti, M. R., Mawassi, M., Valkov, N., Bar-Joseph, M., Moreno, P., Dawson, W. O., 2000. The p20 gene product of Citrus tristeza virus accumulates in the amorphous inclusion bodies. Virology 274, 246-254.

Gowda, S., Satyanarayana, T., Ayllón, M. A., Albiach-Marti, M. R., Mawassi, M., Rabindran, S., Garusey, S. M., Dawson, W. O., 2001. Characterization of the cis-acting elements controlling subgenomic mRNAs of Citrus tristeza virus: production of positive- and negative-stranded 3'-terminal and positive-stranded 5'-terminal RNAs. Virology 286, 134-151.

Grdzelishvili, V. Z., Chapman, S. N., Dawson, W. O., Lewandowski, D. J., 2000. Mapping of the Tobacco mosaic virus movement protein and coat protein subgenomic RNA promoters in vivo. Virology 275, 177-192.

Hammond-Kosack, K. E., Staskawicz, B. J., Jones, J. D. G., Baulcombe, D. C., 1995. Functional expression of a fungal avirulence gene from a modified Potato virus X genome. Mol. Plant Microbe Interact. 8, 181-185.

Higuchi, R., Krummel, B., Saiki, R. K., 1988. A general method of in vitro preparation and specific mutagenesis of DNA fragments: study of protein and DNA interactions. Nucleic Acids Res. 16, 7351-7367.

Hilf, M. E., Karasev, A. V., Pappu, H. R., Gumpf, D. J., Niblett, C. L., Garnsey, S. M., 1995. Characterization of Citrus tristeza virus subgenomic RNAs in infected tissue. Virology 208, 576-582.

Ion-Nagy, L., Lansac, M., Eyquard, J. P., Salvador, B., Garcia, J. A., Le Gall, O., Hemould, M., Schurdi-Levraud, V., Decroocq, V., 2006. PPV long-distance movement is occasionally permitted in resistant apricot hosts. Virus Res. 120, 70-78.

Johnson, J. A., Bragg, J. N., Lawrence, D. M., Jackson, A. O., 2003. Sequence elements controlling expression of Barley stripe mosaic virus subgenomic RNAs in vivo. Virology 313, 66-80.

Karasev, A. V., 2000. Genetic diversity and evolution of closteroviruses. Annu. Rev. Phytopathol. 38, 293-324.

Karasev, A. V., Boyko, V. P., Gowda, S., Nikolaeva, O. V., Hilf, M. E., Koonin, E. V., Niblett, C. L., Cline, K., Gumpf, D. J., Lee, R. F., Garnsey, S. M., Lewandowski, D. J., Dawson, W. O., 1995. Complete sequence of the Citrus tristeza virus RNA genome. Virology 208, 511-520.

Karasev, A. V., Hilf, M. E., Garnsey, M. E., Dawson, W. O., 1997. Transcriptional strategy of closteroviruses: mapping the 5' termini of the Citrus tristeza virus subgenomic RNAs. J. Virol. 71, 6233-6236.

Kumagai, M. H., Turpen, T. H., Weinzettl, N., della-Cioppa, G., Turpen, A. M., Donson, J., Hilf, M. E., Grantham, G. L., Dawson, W. O., Chow, T. P., Piatak, M., Jr., Grill, L. K., 1993. Rapid, high-level expression of biologically active alpha-trichosanthin in transfected plants by an RNA viral vector. Proc. Natl. Acad. Sci. USA 90, 427-430.

Kumagai, M. H., Donson, J., della-Cioppa, G., Harvey, D., Hanley, K., Grill, L. K., 1995. Cytoplasmic inhibition of carotenoid biosynthesis with virus-derived RNA. Proc. Natl. Acad. Sci. USA 92, 1679-1683.

Kumagai, M. H., Keller, Y., Bouvier, F., Clary, D., Camara, B., 1998. Functional integration of non-native carotenoids into chloroplasts by viral-derived expression of capsanthin-capsorubin synthase in *Nicotiana benthamiana*. Plant J.14, 305-315.

Lansac, M., Eyquard, J. P., Salvador, B., Garcia, J. A., Le Gall, O., Decroocq, V., Schurdi-Levraud, V., 2005. Application of GFP-tagged Plum pox virus to study Prunus-PPV interactions at the whole plant and cellular levels. J. Virol. Methods 129, 125-133.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc. Natl. Acad. Sci. USA 101, 15742-15747.

Mawassi, M., Mietkiewska, E., Hilf, M. E., Ashoulin, L., Karasev., A. V., Gafny, R., Lee, R. F., Garnsey, S. M., Dawson, W. O., Bar-Joseph, M., 1995. Multiple species of defective RNAs in plants infected with Citrus tristeza virus. Virology 214, 264-268.

McCormick, A. A., Kumagai, M. H., Hanley, K., Turpen, T. H., Hakim, I., Grill, L. K., Tuse, D., Levy, S., Levy, R., 1999. Rapid production of specific vaccines for lymphoma by expression of the tumor-derived single-chain Fv epitopes in tobacco plants. Proc. Natl. Acad. Sci. USA 96, 703-708.

Pappu, H. R., Karasev, A. V., Anderson, E. J., Pappu, S. S., Hilf, M. E., Febres, V. J., Eckloff, R. M. G., McCaffery, M., Boyko, V., Gowda, S., Dolia, V. V., Koonin, E. V., Gumpf, D. J., Cline, K.C., Garnsey, S. M., Dawson, W. O., Lee, R. F., Niblett, C. L., 1994. Nucleotide sequence and organization of eight 3' open reading frames of the Citrus tristeza closterovirus genome. Virology 199, 35-46.

Peremyslov, V. V., Hagiwara Y., Dolja, V. V., 1999. HSP70 homolog functions in cell-to-cell movement of a plant virus. Proc. Natl. Acad. Sci. USA 96, 14771-14776.

Pogue, G. P., Lindbo, J. A., Garger, S. J., Fitzmaurice, W. P., 2002. Making an ally from an enemy: plant virology and the new agriculture. Annu. Rev. Phytopathol. 40, 45-74.

Prasher, D. C., Eckenrode, V. K., Ward, W. W., Prendergast, F. G., Cormier, M. J., 1992. Primary structure of the Aequorea victoria green-fluorescent protein. Gene 111, 229-233.

Rabindran, S., Dawson, W. O., 2001. Assessment of recombinants that arise from the use of a TMV-based transient expression vector. Virology 284, 182-189.

Raju, R., Huang, H. V., 1991. Analysis of Sindbis virus promoter recognition in vivo, using novel vectors with two subgenomic mRNA promoters. J. Virol. 65, 2501-2510.

Robertson, C. J., Garnsey, S. M., Satyanarayana, T., Folimonova, S., Dawson, W. O., 2005. Efficient infection of citrus plants with different cloned constructs of Citrus tristeza virus amplified in *Nicotiana benthamiana* protoplasts. Proc. 16$^{th}$ Conf. IOCV, 187-195. IOCV, Riverside, Calif.

Rommens, C. M., Salmeron, J. M., Baulcombe, D. C., Staskawicz, B. J., 1995. Use of a gene expression system based on Potato virus X to rapidly identify and characterize a tomato Pto homolog that controls fenthion sensitivity. Plant Cell 7, 249-257.

Ryan, M. D., King, A. M. Q., Thomas, G. P., 1991. Cleavage of Foot-and-mouth disease virus polyprotein is mediated by residues located within a 19 amino acid sequence. J. Gen. Virol. 72, 2727-2732.

Ryan, M. D., Drew, J., 1994. Foot-and-mouth disease virus 2A oligopeptide mediated cleavage of an artificial polyprotein. EMBO J. 13, 928-933.

Sablowski, R. W., Baulcombe, D. C., Bevan, M., 1995. Expression of a flower-specific Myb protein in leaf cells using a viral vector causes ectopic activation of a target promoter. Proc. Natl. Acad. Sci. USA 92, 6901-6905.

Satyanarayana, T., Gowda, S., Boyko, V. P., Albiach-Marti, M. R., Mawassi, M., Navas-Castillo, J., Karasev, A. V., Doija, V., Hilf, M. E., Lewandowski, D. J., Moreno, P., Bar-Joseph, M., Gamsey, S. M., Dawson, W. O., 1999. An engineered closterovirus RNA replicon and analysis of heterologous terminal sequences for replication. Proc. Natl. Acad. Sci. USA 96, 7433-7438.

Satyanarayana, T., Gowda, S., Mawassi, M., Albiach-Marti, M. R., Ayllón, M. A., Robertson, C., Garmsey, S. M., Dawson, W. O., 2000. Closterovirus encoded HSP70 homolog and p61 in addition to both coat proteins function in efficient virion assembly. Virology 278, 253-265.

Satyanarayana, T., Bar-Joseph, M., Mawassi, M., Albiach-Marti, M. R., Ayllón, M. A., Gowda, S., Hilf, M. E., Moreno, P., Garmsey, S. M., Dawson, W. O., 2001. Amplification of Citrus tristeza virus from a cDNA clone and infection of citrus trees. Virology 280, 87-96.

Satyanarayana, T., Gowda, S., Ayllón, M. A., Albiach-Marti, M. R., Rabindran, S., Dawson, W. O., 2002. The p23 protein of Citrus tristeza virus controls asymmetrical RNA accumulation. J. Virol. 76, 473-483.

Satyanarayana, T., Gowda, S., Ayllón, M. A., Dawson, W. O., 2003. Frameshift mutations in infectious cDNA clones of Citrus tristeza virus: a strategy to minimize the toxicity of viral sequences to *Escherichia coli*. Virology 313, 481-491.

Scholthof, H. B., 1999. Rapid delivery of foreign genes into plants by direct rub-inoculation with intact plasmid DNA of a Tomato bushy stunt virus gene vector. J. Virol. 73, 7823-7829.

Scholthof, H. B., Scholthof, K. B., Jackson, A. O., 1995. Identification of Tomato bushy stunt virus host-specific symptom determinants by expression of individual genes from a Potato virus X vector. Plant Cell 7, 1157-1172.

Shivprasad, S., Pogue, G.P., Lewandowski, D. J., Hidalgo, J., Donson, J., Grill, L. K., Dawson, W. O., 1999. Heterologous sequences greatly affect foreign gene expression in Tobacco mosaic virus-based vectors. Virology 255, 312-323.

Takamatsu, N., Ishikawa, M., Meshi, T., Okada, Y., 1987. Expression of bacterial chloramphenicol acetyltransferease gene in tobacco plants mediated by TMV-RNA. EMBO J. 6, 307-311.

Van Vloten-Doting, L., Bol, J. F., Comelissen, B., 1985. Plant virus-based vectors for gene transfer will be of limited use because of the high error frequency during viral RNA synthesis. Plant Mol. Biol. 4, 323-326.

Yusibov, V., Shivprasad, S., Turpen, T. H., Dawson, W., Koprowski, H., 1999. Plant viral vectors based on tobamoviruses. Curr. Top. Microbiol. Immunol. 240, 81-94.

TABLE 1

Lengths of BYV CP sgRNA CE fragments used for engineering of constructs pGEM-BC1/GFP through pGEM-BC7/GFP and pCTV-BC1/GFP through pCTV-BC7/GFP

| Construct name | Inserted fragment of BYV CP sgRNA CE |
|---|---|
| pGEM-BC1, pCTV-BC1 | 13499-13635, 137 nts |
| pGEM-BC2, pCTV-BC2 | 13511-13635, 125 nts |
| pGEM-BC3, pCTV-BC3 | 13523-13635, 113 nts |
| pGEM-BC4, pCTV-BC4 | 13535-13635, 101 nts |
| pGEM-BC5, pCTV-BC5 | 13547-13635, 89 nts |
| pGEM-BC6, pCTV-BC6 | 13559-13635, 77 nts |
| pGEM-BC7, pCTV-BC7 | 13571-13635, 65 nts |

What is claimed is:

1. A method of transfecting a citrus tree with a gene of interest having a 5' end and 3' end, said method comprising inoculating said citrus tree with a sample comprising at least one Citrus tristeza virus (CTV) vector engineered to comprise a construct comprising a heterologous gene of interest, said gene of interest having a 5' end and a 3' end; and a heterologous subgenomic RNA (sgRNA) control element (CE) positioned upstream of the 5' end of said gene of interest such that the sgRNA CE controls expression of the gene of interest, wherein said construct is inserted between CPm and CP genes of the CTV vector; and growing said inoculated citrus tree under conditions to allow a systemic infection of said citrus tree with said at least one CTV vector; wherein expression of said gene of interest occurs for at least two years in the citrus tree with a majority of virus in the systemic infection comprising said CTV vector.

2. The method of claim 1, wherein said sgRNA CE is BYV CP sgRNA CE.

3. The method of claim 1, wherein said gene of interest encodes an antimicrobial polypeptide.

4. The method of claim 1, wherein said inoculating comprises grafting a portion of infected plant tissue to said citrus tree.

5. A citrus tree comprising a systemic infection with a Citrus tristeza virus (CTV) population, wherein at least a portion of said CTV virus population comprises CTV vector having a construct that comprises a heterologous gene of interest, said gene of interest having a 5' end and a 3' end; and a heterologous subgenomic RNA (sgRNA) control element (CE) positioned upstream of the 5' end of said gene of interest such that the sgRNA CE controls expression of the gene of interest, wherein a majority of said CTV virus population is comprised of said CTV vector, and wherein said tree expresses said gene of interest for at least two years; and wherein said construct is inserted between CPm and CP genes of the CTV vector.

6. The citrus tree of claim 5, wherein said citrus tree has been inoculated with said CTV vector under field conditions.

7. The citrus tree of claim 5, wherein said sgRNA CE is Beet yellows virus (BYV) major coat protein (CP) sgRNA CE.

8. The citrus tree of claim 5, wherein said gene of interest encodes an antimicrobial polypeptide.

9. A Citrus tristeza virus (CTV) vector engineered to comprise a heterologous gene of interest, said gene of interest having a 5' end and a 3' end; and an additional heterologous sgRNA CE positioned upstream of the 5' end of said gene of interest such that the CE controls expression of the gene of interest; wherein said heterologous gene of interest and additional heterologous sgRNA CE is inserted between CPm and CP genes of the CTV vector.

10. The vector of claim 9, wherein said additional sgRNA CE is BYV CP sgRNA CE.

11. The vector of claim 9, wherein said gene of interest encodes an antimicrobial polypeptide.

12. A method of producing a citrus tree expressing a gene of interest, the method comprising grafting a portion of the citrus tree of claim 5 with another citrus tree.

13. The method of claim 12, wherein said heterologous sgRNA CE is BYV CP sgRNA CE.

* * * * *